US009681804B2

(12) United States Patent
Spitzer

(10) Patent No.: US 9,681,804 B2
(45) Date of Patent: Jun. 20, 2017

(54) HYBRID LENS SYSTEM FOR HEAD WEARABLE DISPLAY

(71) Applicant: Google Inc., Mountain View, CA (US)

(72) Inventor: Mark B. Spitzer, Sharon, MA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 14/744,641

(22) Filed: Jun. 19, 2015

(65) Prior Publication Data

US 2016/0198949 A1    Jul. 14, 2016

Related U.S. Application Data

(60) Provisional application No. 62/102,491, filed on Jan. 12, 2015.

(51) Int. Cl.
*G02B 27/01* (2006.01)
*A61B 3/11* (2006.01)
(Continued)

(52) U.S. Cl.
CPC .......... *A61B 3/111* (2013.01); *G02B 27/0093* (2013.01); *G02B 27/0172* (2013.01);
(Continued)

(58) Field of Classification Search
CPC ................ G02B 27/01; G02B 27/0101; G02B 27/0107; G02B 27/0132; G02B 27/017;
(Continued)

(56) References Cited

U.S. PATENT DOCUMENTS 3,436,151 A * 4/1969 Conrose, Sr. .......... G02C 5/001
33/262
5,090,796 A * 2/1992 Feinbloom ............... A61B 3/04
351/158
(Continued)

FOREIGN PATENT DOCUMENTS

WO    WO 96-13194 A1    5/1996

OTHER PUBLICATIONS

Missig et al., "Diffractive optics applied to eyepiece design", Applied Optics, vol. 34, Issue 14, pp. 2452-2461, May 10, 1995.
PCT/US2016/013039—International Search Report and Written Opinion, mailed Apr. 29, 2016, 10 pages.

*Primary Examiner* — Stephone B Allen
*Assistant Examiner* — Rahman Abdur
(74) *Attorney, Agent, or Firm* — Blakely Sokoloff Taylor & Zafman LLP

(57) ABSTRACT

A hybrid optical system for a head wearable display includes a central vision lens and a peripheral vision lens. The central vision lens approximately aligns with a cornea of a user to provide lensing to a central vision of the user when the user is looking straight forward. The peripheral vision lens, different than the central vision lens, provides lensing to an extended field of view that extends angularly beyond the central vision lensed by the central vision lens when the user is looking straight forward. The peripheral vision lens is disposed around the central vision lens. The peripheral vision lens has a co-incident optical center with the central vision lens but the central vision lens is offset from a physical center of the peripheral vision lens.

24 Claims, 16 Drawing Sheets

(51) Int. Cl.
*G02B 27/00* (2006.01)
*G02B 3/08* (2006.01)

(52) U.S. Cl.
CPC ........ *G02B 3/08* (2013.01); *G02B 2027/0132* (2013.01); *G02B 2027/0174* (2013.01)

(58) Field of Classification Search
CPC ............ G02B 27/0172; G02B 27/0178; G02B 27/0181; G02B 27/0183; G02B 27/0185; G02B 27/0189; A61B 3/11
USPC ............ 351/159.42, 159.41, 159.47, 159.48, 351/159.51, 159.52
See application file for complete search history.

(56) References Cited

U.S. PATENT DOCUMENTS

| | | | |
|---|---|---|---|
| 5,129,717 A * | 7/1992 | Feinbloom | G02B 7/002 351/158 |
| 6,804,066 B1 | 10/2004 | Ha et al. | |
| 2004/0223116 A1 | 11/2004 | Baugh | |
| 2007/0091250 A1 | 4/2007 | Hwang | |
| 2009/0046349 A1* | 2/2009 | Haddock | G02B 5/1895 359/319 |
| 2014/0125944 A1* | 5/2014 | Huang | B29D 11/0048 351/159.33 |
| 2014/0268017 A1* | 9/2014 | Sweis | G02C 11/10 351/158 |

* cited by examiner

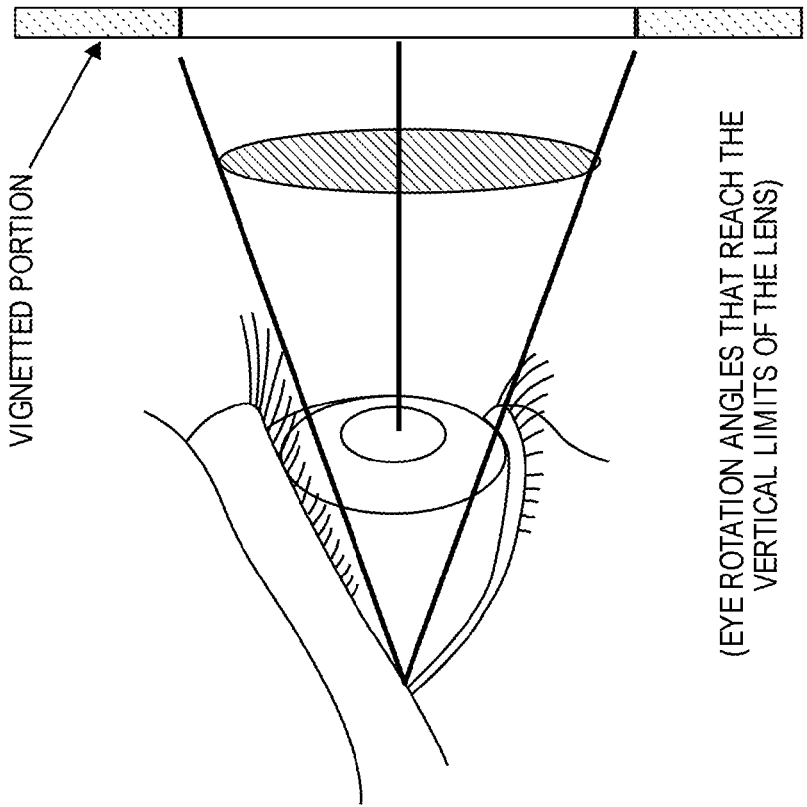
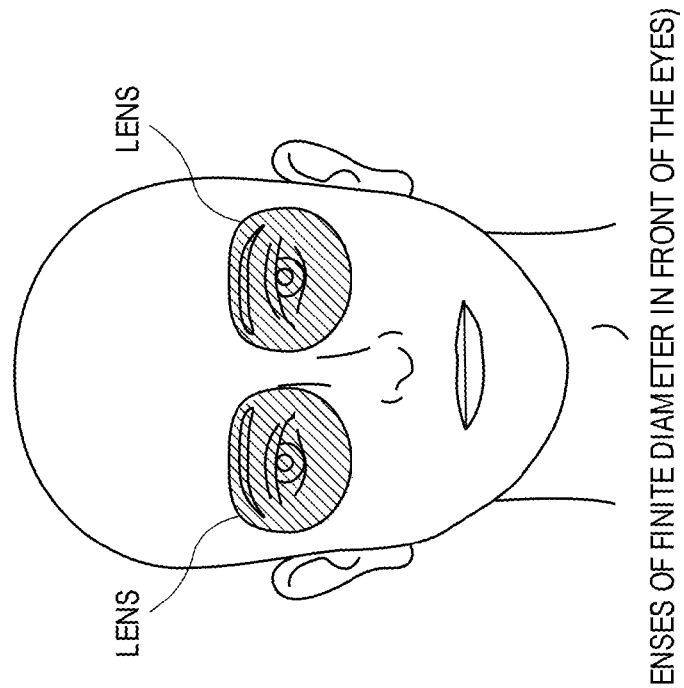
FIG. 4

(RIGHT EYE ILLUSTRATES ANGLE AVAILABLE TO THE EYE VIA ROTATION)

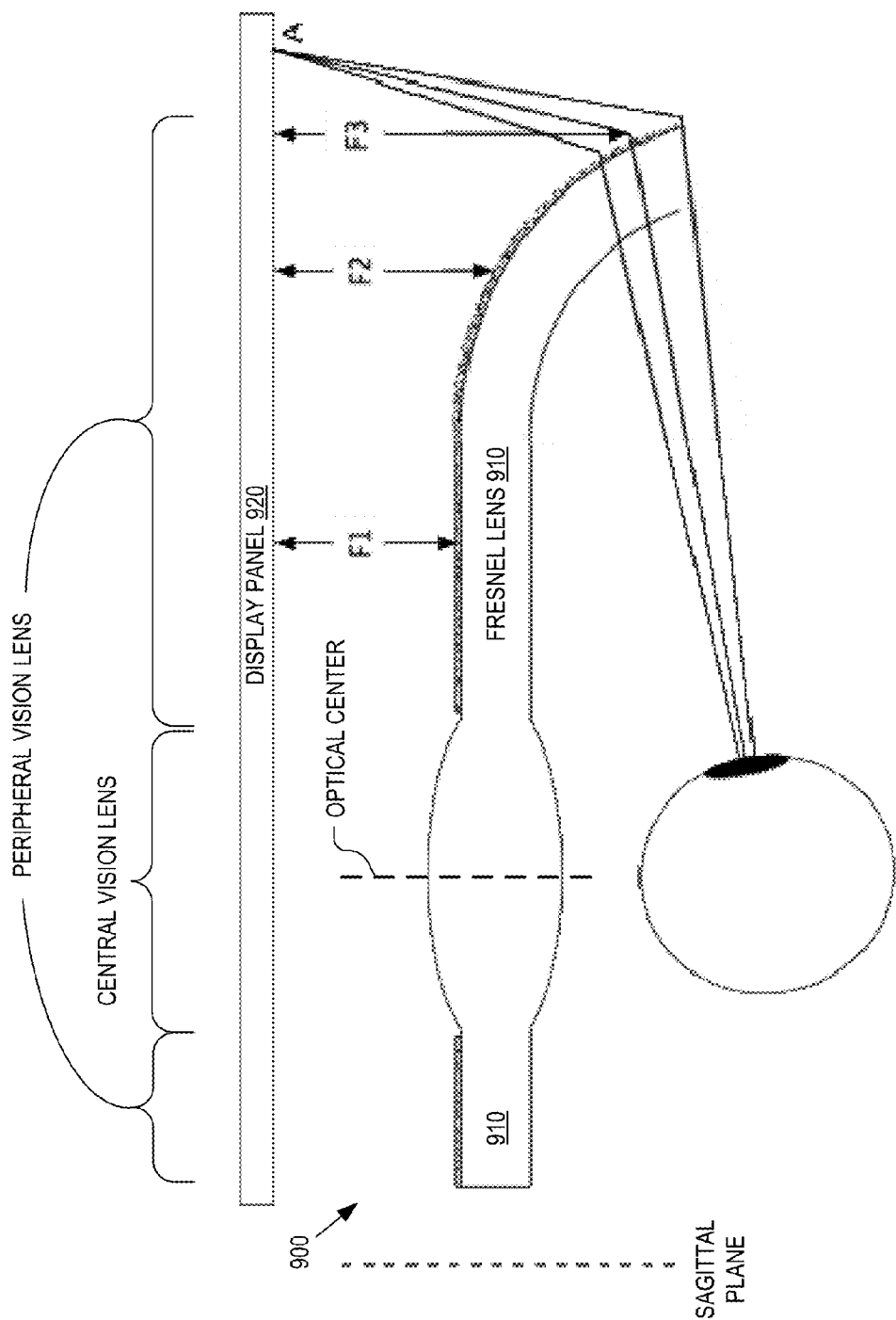

HYBRID LENS SYSTEM FOR HEAD WEARABLE DISPLAY

CROSS-REFERENCE TO RELATED APPLICATION

This application claims priority to U.S. Provisional Application No. 62/102,491 filed on Jan. 12, 2015, the contents of which are incorporated herein by reference.

TECHNICAL FIELD

This disclosure relates generally to optical systems, and in particular but not exclusively, relates to optical systems for head wearable displays.

BACKGROUND INFORMATION

A head mounted display ("HMD") or head wearable display is a display device worn on or about the head. HMDs usually incorporate some sort of near-to-eye optical system to create a magnified virtual image placed between a meter or so (near) and optical infinity (distant) in front of the user. Single eye displays are referred to as monocular HMDs while dual eye displays are referred to as binocular HMDs. Some HMDs only permit the user to see a display image (e.g., computer generated image, still image, video image, etc.) while other types of HMDs are capable of superimposing the display image over a real-world view. The type of HMD that shows a real-world view combined with a display image typically includes some form of see-through eyepiece and can serve as the hardware platform for realizing augmented reality. With augmented reality the viewer's perception of the world has added to it an overlaying display image. This type of system is sometimes also referred to as a head-up display ("HUD"). Fully immersive displays (i.e., not see-through) are often referred to as virtual reality ("VR") displays. Immersive HMDs can also provide augmented reality by electronically combining images from a camera or other sensors that are viewing the world in front of the user, fused with other electronic imagery or information.

HMDs have numerous practical and leisure applications. Aerospace applications permit pilots to see vital flight control information without taking their eyes from the flight path. Public safety applications include tactical displays of maps and thermal imaging. Other application fields include video games, transportation, and telecommunications. There are certain to be newly found practical and leisure applications as the technology evolves; however, many of these applications are limited due to the cost, size, weight, field of view, and efficiency of conventional optical systems used to implement existing HMDs.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

FIG. 4 illustrates how edges of a lens vignette or limit a user's view.

FIG. 9A illustrates a hybrid lens system, in accordance with a fourth embodiment of the disclosure.

DETAILED DESCRIPTION

Embodiments of an apparatus, system, and method of operation for a hybrid optical system that uses both an aspherical lens for foveal perception and a Fresnel lens for peripheral vision to provide a wide field of view suitable for head wearable displays are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

This disclosure is separated into two parts. Part 1, including FIGS. 1-5, sets forth various terms along with general concepts relevant to the optical design of head wearable displays. Part 2, including FIGS. 6-14, sets forth various embodiments of a hybrid optical system suitable for a head wearable display that supports a high quality immersive visual user experience. An example high quality visual immersive user experience is one that generates a true feeling of presence, at a level where the user suspends disbelief. It is well known that the optics and related visual experience are not the only requirements for suspension of disbelief; however, this disclosure has a primary focus on the visual experience provided by the optics and display. Attributes of an optical system that achieve this may include: 20:20 vision in the user's primary field of view (e.g., a cone of 60 degrees for each eye), a full horizontal field of view approaching 180 degrees, and a vertical field of view approaching 100 degrees. The embodiments disclosed below in part 2 illustrate how some or all of these attributes can be achieved with a hybrid optical system that is well-matched to the requirements of human vision.

Part 1: Terminology & Design Concepts

A. Inter-pupillary Distance Considerations

Figure 1:
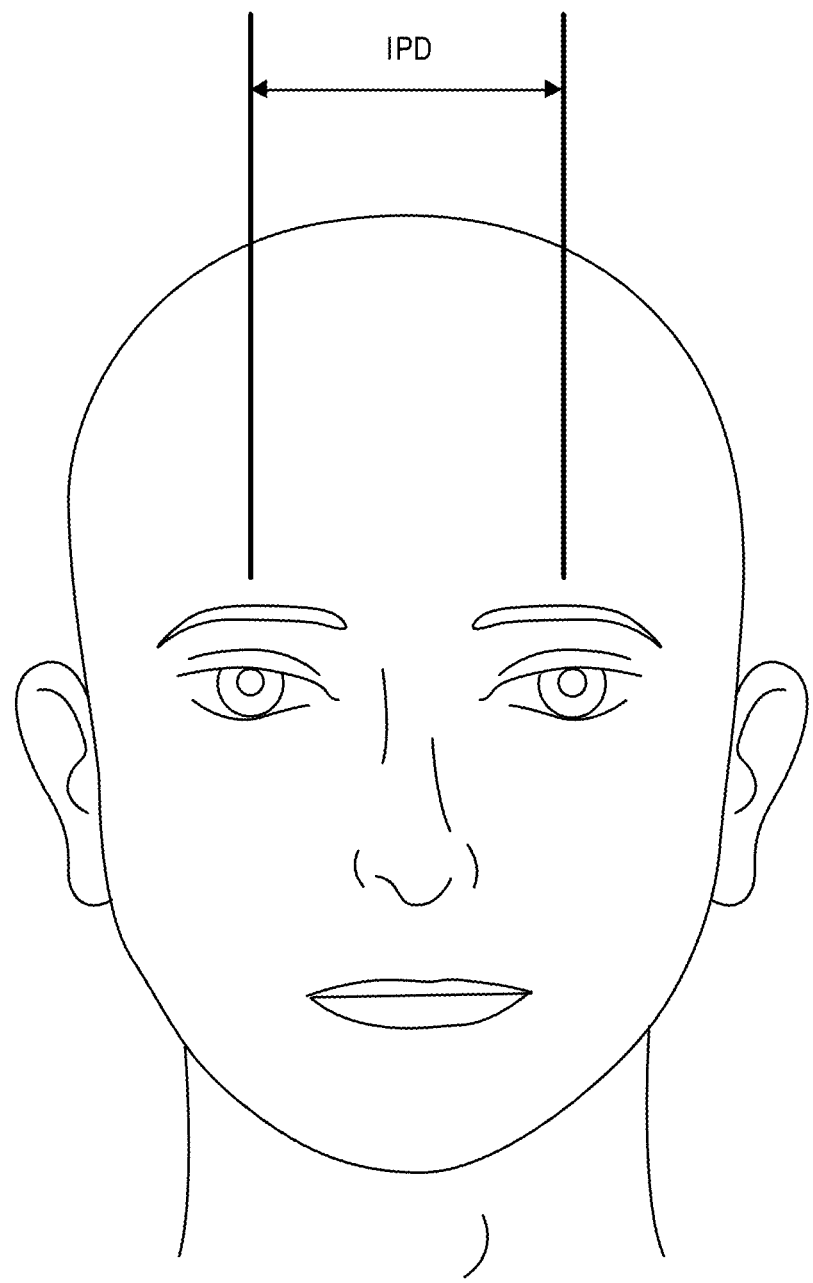
FIG. 1 illustrates the concept of an inter-pupillary distance (IPD).

Human inter-pupillary distance (IPD) is defined as the distance between the centers of the pupils of the left and right eyes (see FIG. 1). The right and left lenses of a binocular display also have centers, and the distance between lens centers can be defined as the IPD of the optical system. An analysis of display and optics requirements may begin with considerations of whether a system will have adjustable IPD or fixed IPD to match the IPD of a user. Adjustable system IPD may offer a good user fit, but is typically more costly, heavier, and more prone to misalignment issues owing to moving parts. Fixed IPD may not provide as satisfying visual experience for every user, but is typically more comfortable and more affordable. The systems may also be sold in multiple SKUs, each with a different fixed IPD value that works over a limited range, so that a user may choose the IPD that is the best fit. The details of the optics determine the range of IPD that a particular design will fit.

Human IPD ranges from 52 mm to 75 mm for most of the adult population. Therefore, to fit the narrowest likely adult IPD, we have 26 mm between the pupil and the mid-sagittal frontal plane (see FIG. 2). For adjustable system IPD over this range, this also sets the radius of a conventional round positive lens to a maximum of 26 mm. (The lens may need a cut-out for the nose if the lens is close to the face.) It will become evident later in the discussion that this radius limits the horizontal field of view (FOV) of the display owing to vignetting. It is desirable to overcome this FOV limitation.

B. Visual Acuity and Pixel Size

A Snellen visual acuity of 20:20 corresponds to an angular resolution of 1 minute of arc. Visual acuity of 20:40 corresponds to a resolution of 2 minutes of arc. For a person with normal vision (20:20), the retina cannot distinguish a difference between an emitting object subtending 1 min of arc and an emitting object subtending less than 1 min of arc. Therefore, for a person with 20:20 vision, any image of a pixel (which is an emitting object) that subtends less than 1 minute of arc will nevertheless be perceived as subtending 1 minute of arc, owing to the size and spacing of the cones on the retina. Therefore, if designing for 20:20 acuity, there are few reasons to design systems that employ pixels whose images subtend less than 1 min of arc.

A second factor related to visual acuity is the quality of the optical system. In order to create a system that delivers 20:20 vision, the optical system should be capable of providing magnification without blurring pixels that are separated by only 1 min of arc. However, very high performance lenses are often very narrow in diameter and thus not well suited to a wide FOV system. A wide FOV is desirable in a head wearable display.

C. Binocular Overlap

Figure 2:
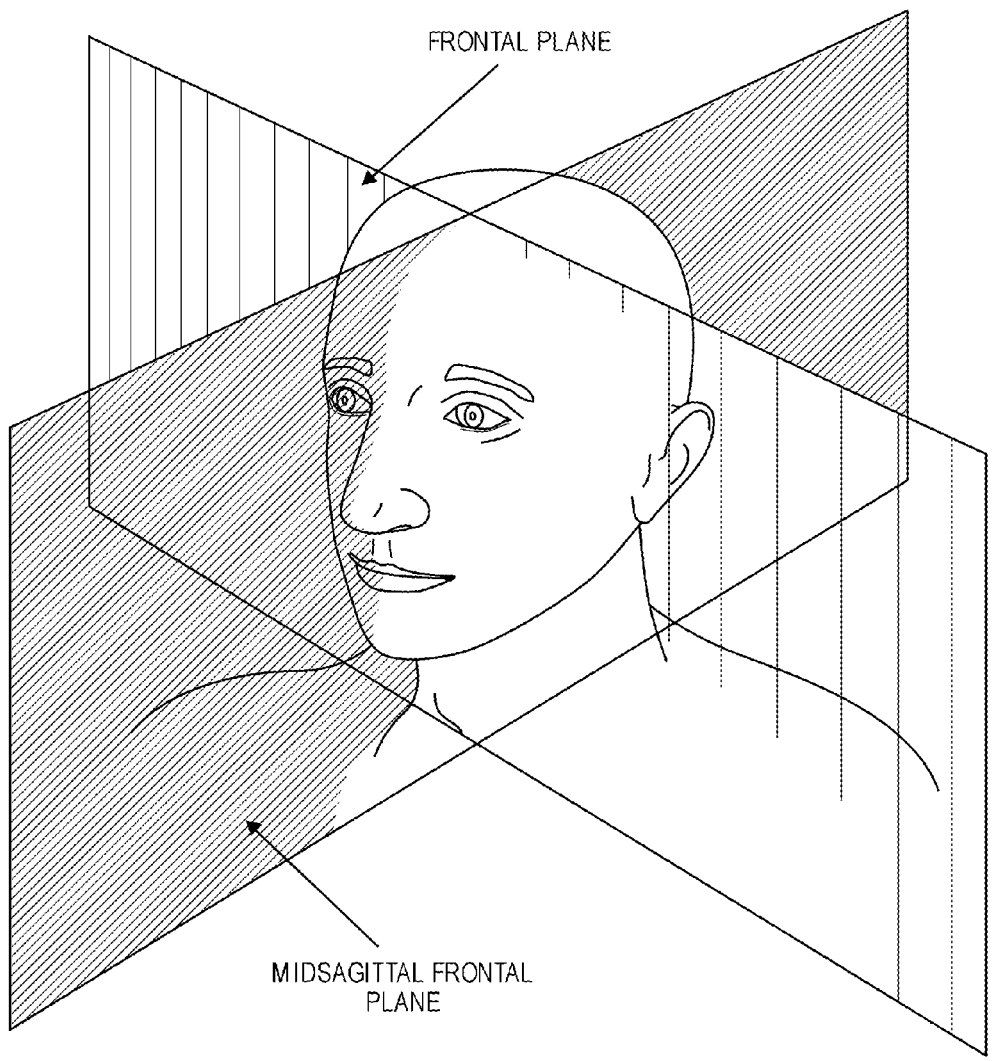
FIG. 2 illustrates the concept of a sagittal plane.

In binocular displays, individual virtual images are created for the left and right eyes by a left display and lens, and a right display and lens. The left and right virtual images may completely or partially overlap, depending on the FOV of the optics. The binocular overlap region is defined as the region of the left and right virtual images that overlap geometrically. FIG. 2 illustrates the midsagittal frontal plane (referred to hereafter simply as the sagittal plane) that bisects the horizontal visual field. The left eye, the left optics, and the left display are on the left side of the sagittal plane, and the right eye, right optics, and right display are on the right side of the sagittal plane. However, the two virtual images created by the optics and displays generally cross the sagittal plane. Thus, when viewing the virtual images, the left or right eye gaze may (and often does) cross the sagittal plane.

Figure 3:
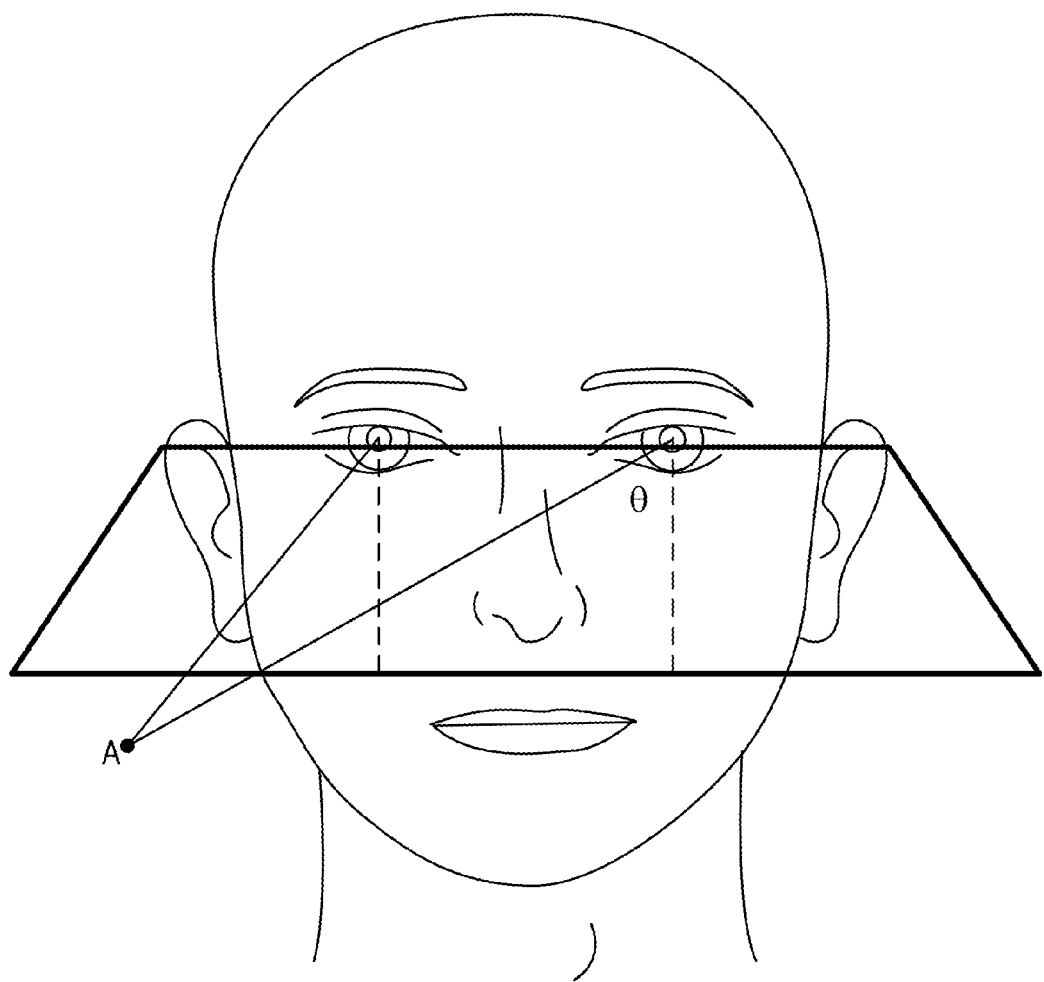
FIG. 3 is an illustration of a binocular view of an object not having extent on the sagittal plane.

The binocular overlap region is limited on the left by the edge of the virtual image perceived by the right eye looking left across the sagittal plane, and limited on the right by the edge of the virtual image perceived by the left eye looking right across the sagittal plane. FIG. 3 illustrates an example of the two eyes viewing an object at point A in the right visual field. The left eye is turned to an angle, θ, to view point A. If point A is created by the right-most pixel on the left-eye display, then the half angle denoting the edge of the binocular overlap region is θ, and by symmetry the field of view of the binocular overlap region is twice θ. In other words, point A lies on the right edge of the virtual image created by the left eye display. A corresponding point at −θ lies on the left edge of the virtual image created by the right eye display. Therefore the binocular overlap is 2θ.

The eye turns comfortably over a range of 0 to 15 degrees in any direction. Accounting for a further 2.5 degrees for half the foveal region, the lower acceptable value of θ is about 18 degrees. However, 18 degrees may be too narrow to establish a satisfactory degree of presence. To allow even further eye motion into an uncomfortable but useful range, a more desirable value for θ is 30 degrees, and an upper useful value is likely about 45 degrees (it may vary from person to person).

Once the value of θ is chosen, the number of pixels in the half angle region needed for 20:20 acuity can be determined by dividing the half angle by the pixel subtense. For example, if the half angle is 30 degrees, the number of pixels in the half angle is 1800. For the full 60 degree FOV in the binocular overlap region, 3600 pixel columns should be in the display. For θ of 45 deg, 2700 pixel columns should be between the eye and the sagittal plane to fill the half angle region, and 5400 are needed for a 90 degree binocular overlap region.

Another design consideration is whether the full binocular overlap region is to have 20:20 visual acuity. This seems desirable but may not be necessary. Thus, a system could be designed with a 90 degree binocular overlap, but with visual acuity of 20:20 only over a 60 degree overlap sub-region. Thus, an optical system that provides high acuity over a central region of the binocular overlap region and a lower acuity at angles beyond this central region can be desirable.

HMDs with head tracking make it unnecessary for the eye to turn beyond a comfortable range to view an object that is not in the central visual field. The head and the eye can thus turn to place the image of the object of interest on the fovea. Since the retina has diminishing cone density as the distance from the fovea increases, an HMD system intended for VR need not provide high resolution at all field angles. By taking account of the human visual system in this way, the HMD system may be simplified (in a manner to be shown), without significant loss of presence.

D. Focal Length

Another design factor is the focal length of the optical system, which determines the magnification. Ignoring for the moment vignetting which can limit FOV, horizontal FOV (H-FOV) of the image approximately satisfies the following equation:

$$H\text{-}FOV=2*\arctan(\text{image width}/2F),$$

where F is the focal length, or $$F=(\text{image width}/2)/\tan(H\text{-}FOV/2).$$

For a system with 20:20 acuity and pixel subtense of 1 min, this equation defines the relationship between the pixel size and the focal length. Since $\tan(0.5 \text{ min})=0.000145$, $$F=\text{pixel width}/0.00029.$$

A 10 micron pixel therefore calls for a focal length of 34 mm in order for the 10 micron pixel to subtend 1 min of arc.

E. Vignetting

Although the FOV of the image is set by the focal length and display size, the display may be vignetted by the optical system. FIG. 4 illustrates how the view can be limited (vignetted) by the edge of the lens. The image is viewed through the lens which constitutes an aperture, and if the display is made sufficiently large, the edges of the display will not be viewable through the lens, and outer parts of the image cannot be seen, as shown in FIG. 4. When considering eye rotation as part of the vignetting of the fovea, the radius of the eye should be considered (because the pupil moves during eye rotation). When using the radius of the eye in determining vignetting angles, a simplifying assumption can be made that the center of the eye is also the center of eye rotation. Though not strictly correct, this assumption is close enough for an accurate estimate of vignetting.

Figure 5:
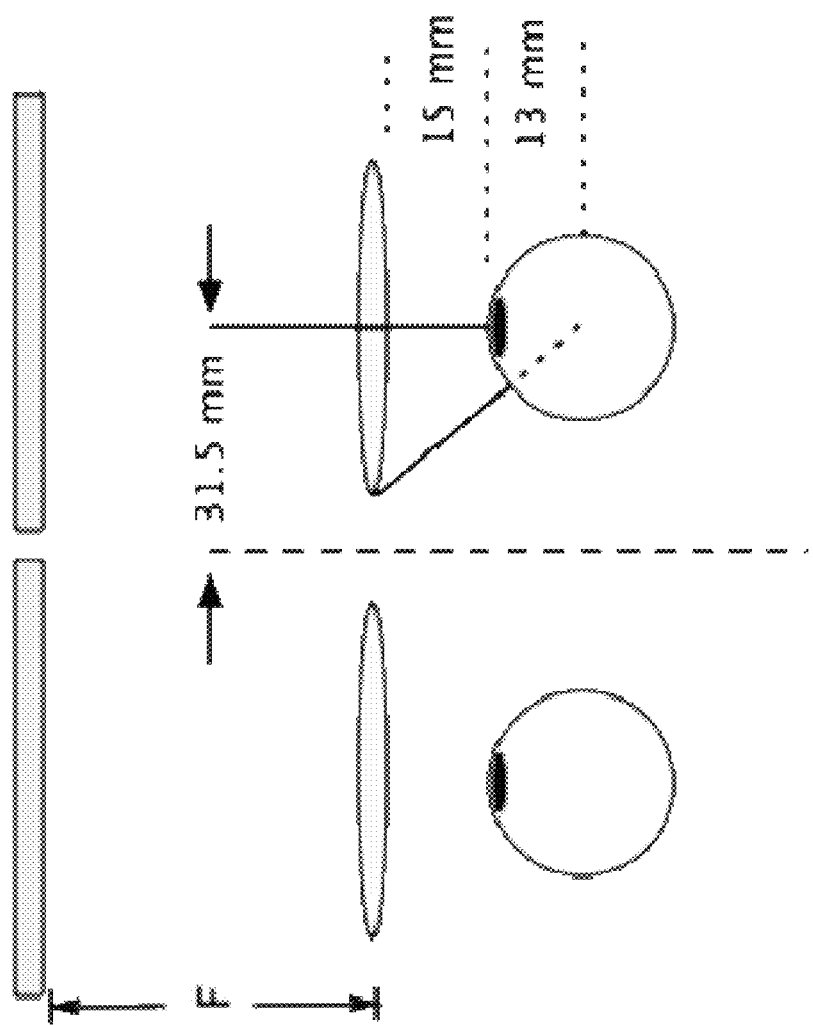
FIG. 5 illustrates how eye relief impacts the degree of vignetting by a lens.

A critical distance for determining the degree of vignetting by the lens is the distance from the eye to the lens (termed "eye relief") plus the eye radius (nominally 13 mm). A close practical eye relief is about 15 mm, thus the sum is 28 mm. FIG. 5 shows the implications for the median IPD of 63 mm. The distance from the eye to the sagittal plane is 31.5 mm. The maximum radius of the lens is thus 31.5 mm for the median case, and assuming we need 1 mm for a lens-supporting ring, the maximum radius is 30.5 mm. The angle is given by arctan(30.5/28) or 47 deg. If the eye relief is larger (for example, if the system is designed to go over prescription eyewear), this angle may be reduced. For an eye relief of 30 mm, the angle is 35 deg. An optical system that permits the eye to turn beyond its comfortable range without suffering substantial vignetting is desirable.

Part 2: Embodiments of a Hybrid Lens System with Wide FOV

Typical HMD designs are based on a single conventional lens per eye, in which the diameter is approximately equal to or less than the focal length (this is typical of conventional plano-convex and double convex lenses). The edge of the lens limits the FOV of the image owing to vignetting as previously discussed. By eliminating the vignetting imposed by the lens, the FOV can be increased. Embodiments disclosed herein use a hybrid lens system including a Fresnel lens and a refractive spherical or aspherical lens.

FIGS. 6A and 6B illustrate a hybrid lens system 600, in accordance with an embodiment of the disclosure. FIG. 6A is a top cross-sectional illustration while FIG. 6B is a front illustration. The illustrated embodiment of hybrid lens system 600 includes a singlet lens 605 (e.g., spherical or aspherical lens) formed at the optical center of a Fresnel lens 610 (e.g., an aspherical Fresnel lens). In other words, the optical center of singlet lens 605 is co-incident with the optical center of Fresnel lens 610. In the illustrated embodiment, the optical centers of the lenses are placed in front of the user's pupil/cornea (when the eye is gazing straight ahead). In the illustrated embodiment, the central vision lens (e.g., singlet lens 605) is implemented as a refractive lens having two curved surfaces; however, a refractive lens having only a single curved surface may also be implemented. Furthermore, the central vision lens may be implemented as a progressive lens, an achromatic lens, a diffractive optical element, a hologram, or even a hybrid refractive-diffractive lens.

Since an optical system intended for either the left or right eye should not cross the sagittal plane, Fresnel lens 610 is truncated on the nasal side and the physical center of Fresnel lens 610 and its optical center are not co-located (e.g., see FIGS. 6A and 6B). In other words, hybrid lens system 600 extends asymmetrically from the optical center, extending further in the temporal direction than the nasal direction. The vertical extent of hybrid lens system 600 may also be asymmetric. If Fresnel lens 610 and singlet lens 605 have the same focal length, the user will see the same magnification from both lenses.

One reason for replacing the central area of Fresnel lens 610 with singlet lens 605 is the following: for displays of very small pixel pitch, the singlet lens may provide better magnification of high spatial frequencies where it matters most—directly in front of the eye over the limited range of comfortable gaze angles. In this way, the ability to resolve objects subtending 1 min of arc is preserved over the gaze range of the eye by using singlet lens 605, and the remainder of the scene is also presented, although at the resolution permitted by the Fresnel lens 610, which may be less than singlet lens 605. Another way to state this is that Fresnel lens 610 may have a less satisfactory modulation transfer function (MTF) than singlet lens 605, but since Fresnel lens 610 acts mainly outside the central gaze range of the fovea, the reduced MTF may not be significantly consequential. Accordingly, singlet lens 605 serves as a central vision lens while Fresnel lens 810 serves as a peripheral vision lens when the user is looking straight forward.

Referring again to FIG. 6, gaze direction A represents the user's eye looking straight ahead through the optical center of singlet lens 605. Gaze B shows an eye rotation angle (for simplicity, pupil location after rotation is not shown) where the gaze is through the transition region between the singlet lens 605 and the grooved surface of Fresnel lens 610. The transition region, in some embodiments, is in the range of 30 to 45 degrees with respect to straight ahead. Gazed direction C is through Fresnel lens 610. Large gazing angles are possible. Thus, this approach overcomes the vignetting of a conventional lens while preserving the quality of the conventional lens for the most important gaze directions.

It is noteworthy that Fresnel lens 610 (and its lower resultant acuity) is used outside the principal field of gaze, which is acceptable because when the user is looking through singlet lens 605 (whose image is upon the fovea), the Fresnel image is provided to a region of the retina beyond the fovea, and from which the user typically cannot perceive high resolution. Accordingly, an acceptable wide FOV is presented to the user.

A second infrequent case occurs when the eye turns to enable the user's gaze along direction C through Fresnel lens 610, and in this case a lower acuity image is provided to the fovea. However, this is also acceptable since rarely is the eye turned to high angles, and even more rarely can a high angle (e.g., >30 degrees) of eye rotation be sustained without discomfort. Instead, normally the head is turned to view objects so that the eye remains in the comfortable gaze range. When a head wearable display (e.g., a VR display or augmented reality display) includes head tracking, the head will also be turned to view objects at high initial angles, so that gaze C direction will be converted to gaze A direction via head motion. For these reasons, user dissatisfaction with low acuity at high eye rotation angles is expected to be rare.

Figure 6:
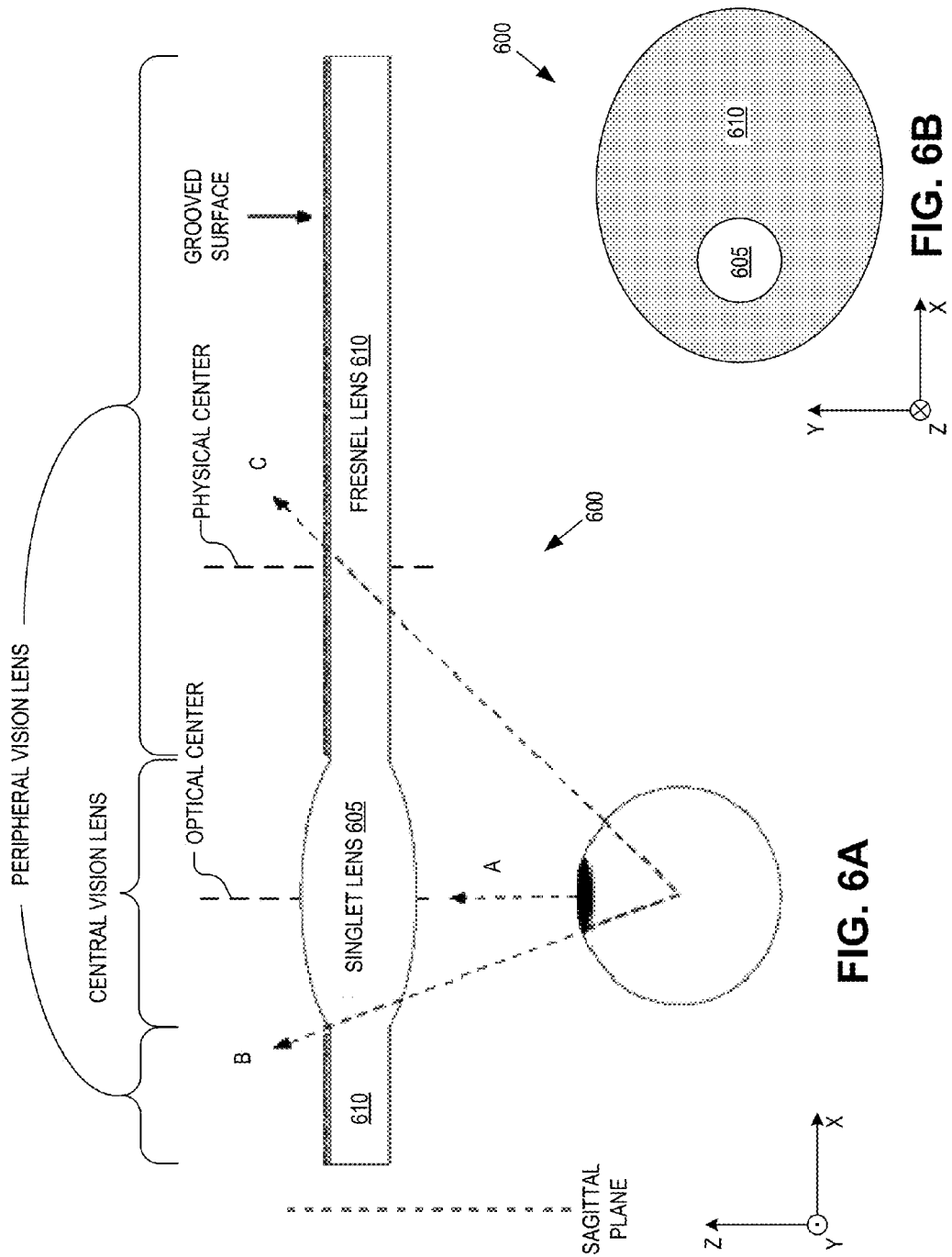
FIGS. 6A & 6B illustrate a hybrid lens system, in accordance with a first embodiment of the disclosure.

FIG. 6 illustrates a singlet spherical or aspherical lens 605 formed integrally (such as by injection or compression molding) at the optical center of Fresnel lens 610. Alternatively, a cavity or hole may be provided in Fresnel lens 610 and singlet lens 605 may be inserted and glued by optical techniques known in the art. In other embodiments, Fresnel lens 610 can be molded around a singlet lens 605 of a different material (such as for example glass) using a technique referred to as insert molding.

The extension of Fresnel lens 610 beyond singlet lens 605 toward the nose provides a capability for more binocular overlap than is obtained by singlet lens 605 alone. For example, singlet lens 605 may provide high visual acuity over a 60 degree FOV, and the presence of Fresnel lens 610 extending in the nasal direction may provide an additional amount of binocular overlap, but with lower acuity. Similarly, the vertical field of binocular overlap may be extended as well.

Although FIG. 6A illustrates Fresnel lens 610 having a flat surface facing the eye with the Fresnel grooved surface facing outward (e.g., towards a display panel), the surfaces may be reversed. Additionally, the surface opposite to the Fresnel groove surface may not be flat and may have an aspherical or other corrections or thickness variations to improve the optical performance for gaze directions such as gaze direction C. The design of hybrid lens system 600 may also be optimized to reduce or eliminate artifacts from the transition region between Fresnel lens 610 and singlet lens 605, for example by orienting draft angles of the Fresnel lens grooves to be parallel to gaze direction B. In yet other embodiments, the Fresnel grooves may be present on both opposing surfaces.

Figure 7:
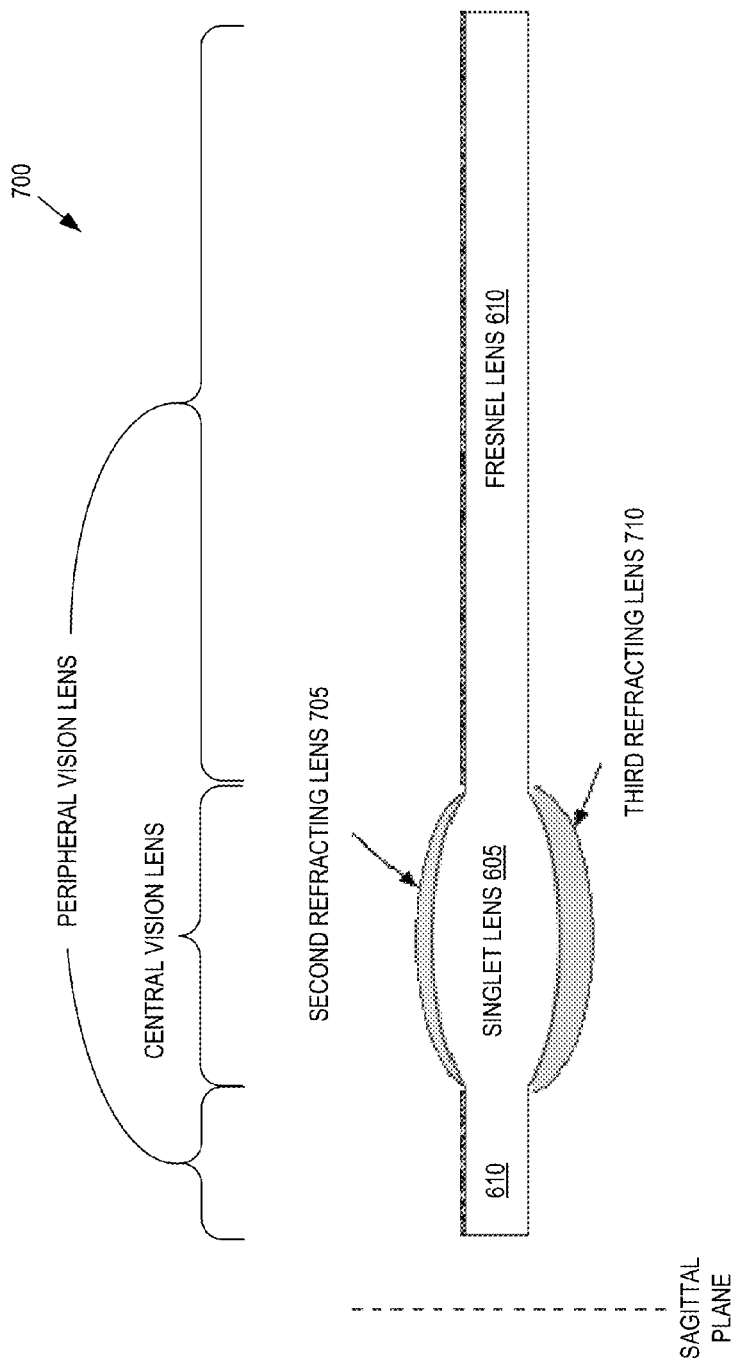
FIG. 7 illustrates a hybrid lens system, in accordance with a second embodiment of the disclosure.

FIG. 7 illustrates a hybrid lens system 700, in accordance with an embodiment of the disclosure. Hybrid lens system 700 includes a second refracting lens 705 and/or third refracting lens 710 added adjacent to singlet lens 605 to correct chromatic aberration, distortion, or resolve other aberrations. Although FIG. 7 illustrates lenses 705 and 710 as meniscus lenses, these additional lensing layers over the frontside or backside of singlet lens 605 may be positive or negative lenses depending on the requirements of the optical design. Thus, the complete central vision lens may be a singlet, doublet, triplet or other structure that comprises positive or negative surfaces that may be spherical, aspherical or even progressive (as will be discussed later). The illustrated peripheral vision lens is Fresnel lens 610.

Figure 8:
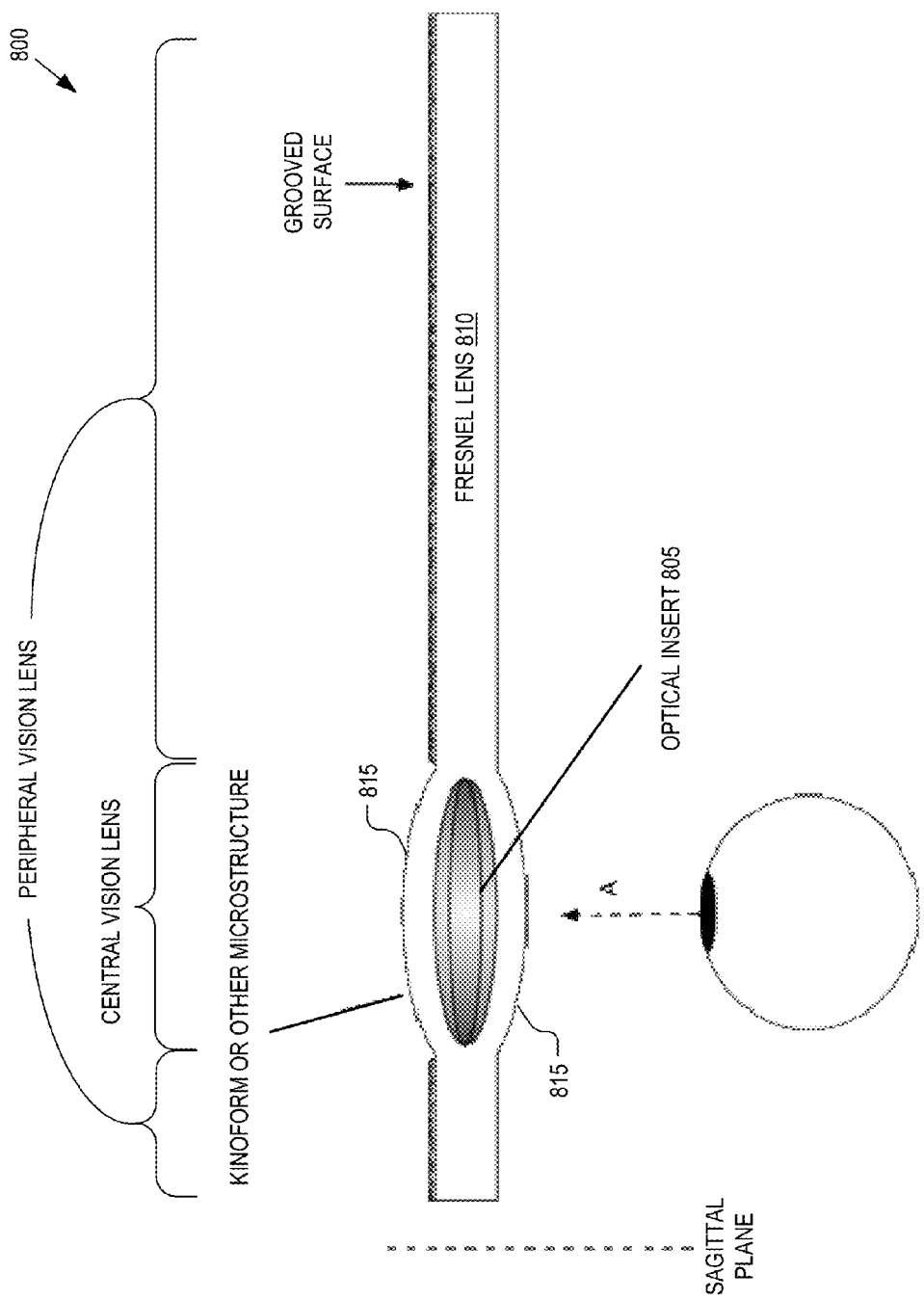
FIG. 8 illustrates a hybrid lens system, in accordance with a third embodiment of the disclosure.

FIG. 8 illustrates a hybrid lens system 800, in accordance with an embodiment of the disclosure. Hybrid lens system 800 is formed using an insert molding technique in which a plastic material (such as polymethyl methacrylate) is formed around an optical insert 805, such as a glass singlet, doublet, or triplet lens, or otherwise. Thus, optical insert 805 (central vision lens) is formed of a different material than Fresnel lens 810 (peripheral vision lens). Note that the Fresnel lens 810, or a microstructure such as a kinoform or a diffractive optical element, may be formed over the outer surfaces 815 that encapsulate optical insert 805.

An optical system intended for use in a very high field of view system can also be formed from a hybrid lens system. One way to improve peripheral vision is to employ a curve near the temple as shown in FIG. 9A. By curving Fresnel lens 910, the rays emitted for example by a pixel at point A on display panel 920 may be collected by hybrid optical system 900 and relayed to the eye. In FIG. 9A, the eye is turned to a high angle, but peripheral rays may be seen by the retina in peripheral vision without eye rotation, provided the display and lens produce rays that produce a virtual image in the periphery. Although we show a curve on one axis, Fresnel lens 910 may be curved along multiple axes. In one embodiment, Fresnel lens 910 is formed upon a curved substrate that bends in one or more axes. In the illustrated embodiment, Fresnel lens 910 is planar on the nasal side of the central vision lens but curved along a portion on the temple side of the central vision lens.

Another optional feature is illustrated in FIG. 9A, in which the focal length (e.g., F1, F2, F3) of Fresnel lens 910 varies slowly with radial distance from the optical center of Fresnel lens 910. In one embodiment, the focal length variation is accomplished by slight variations in the slope of the Fresnel grooves of the peripheral vision lens (e.g., Fresnel lens 910). Near the center of Fresnel lens 910, the focal length is F1. As the radius increases, the focal length is slowly and continuously increased to F2 and then F3. If the change in focal length is gradual, the gradient in focal length will have minimal impact on the image on the fovea (meaning on the perception of the image), but the overall effect will be to enable the image to remain in focus, despite the increase in distance between the hybrid optical system 900 and the display panel 920. Accordingly, in one embodiment, the increasing focal length Fresnel lens 910 compensates for the inward curvature of Fresnel lens 910 on the temple side, which results in an increasing separation distances between hybrid optical system 900 and the planar display panel 920. The change in magnification that occurs when the focal length is gradually changed may be reduced by remapping and pre-distorting the image electronically, so that the magnification change is approximately canceled. However, if the change occurs at sufficient distance from the optical center, the change in magnification may not be perceptible.

Many variations of the approach shown in FIGS. 6, 7, 8 and 9 are possible. For example, the central vision lens may include a diffractive optical element or a hologram. Any combination of insert molding steps may be used to form the overall hybrid lens system. Although FIG. 9A shows a bend in one axis, the hybrid lens can also be formed on a spherical, aspherical, or toric base shape. In such a case, the Fresnel groove structure is modified accordingly. For example, the Fresnel grooves may be formed on the eye-ward facing surface of Fresnel lens 910. A variation in focal length may also be employed in the peripheral vision section of the hybrid lens when formed on a two-dimensional curved surface.

Figure 9B:
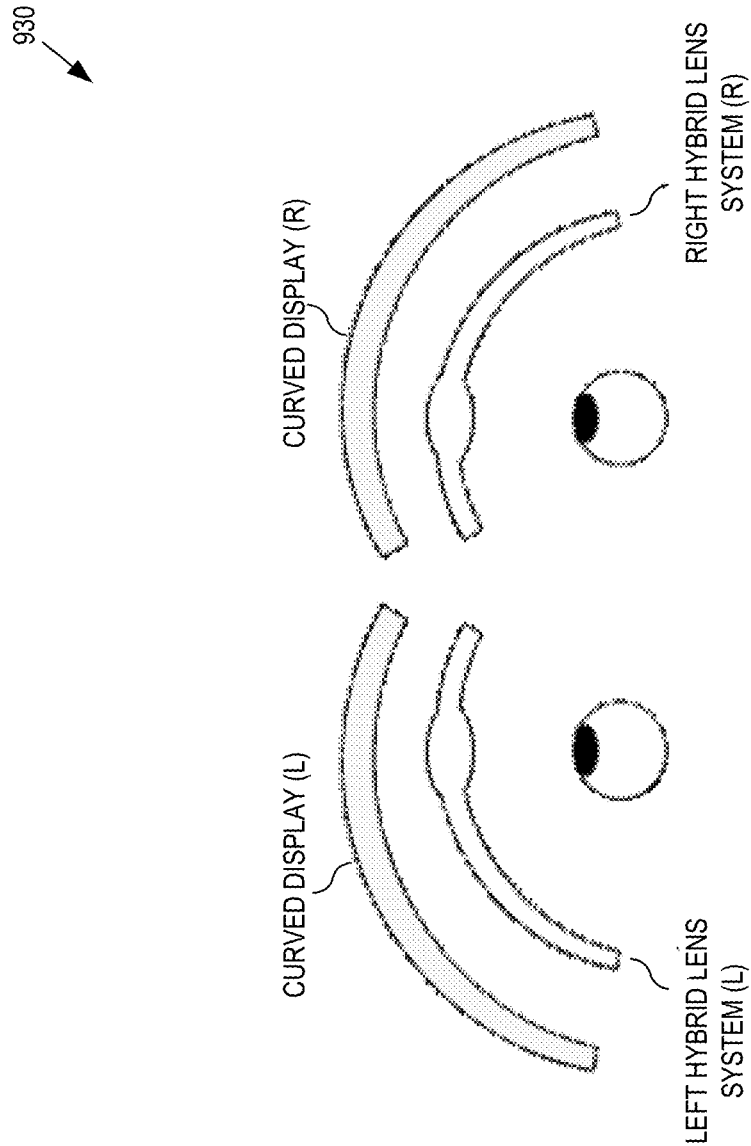
FIG. 9B illustrates a binocular head wearable display including hybrid lens systems and curved displays, in accordance with a fifth embodiment of the disclosure.

The hybrid lens systems described above may also be used with curved displays. The curvature of the hybrid lens may be designed to match the curvature of the display so that high spatial fidelity in the image may be maintained, even in the periphery. In this way it is possible to make very high binocular FOV systems (>180 degrees in the horizontal field) with acuity matching the retina over the entire horizontal, and vertical visual field, or any subset of the entire field. FIG. 9B illustrates a binocular head wearable display 930 including hybrid lens systems and curved displays, in accordance with another embodiment of the disclosure.

Figure 9C:
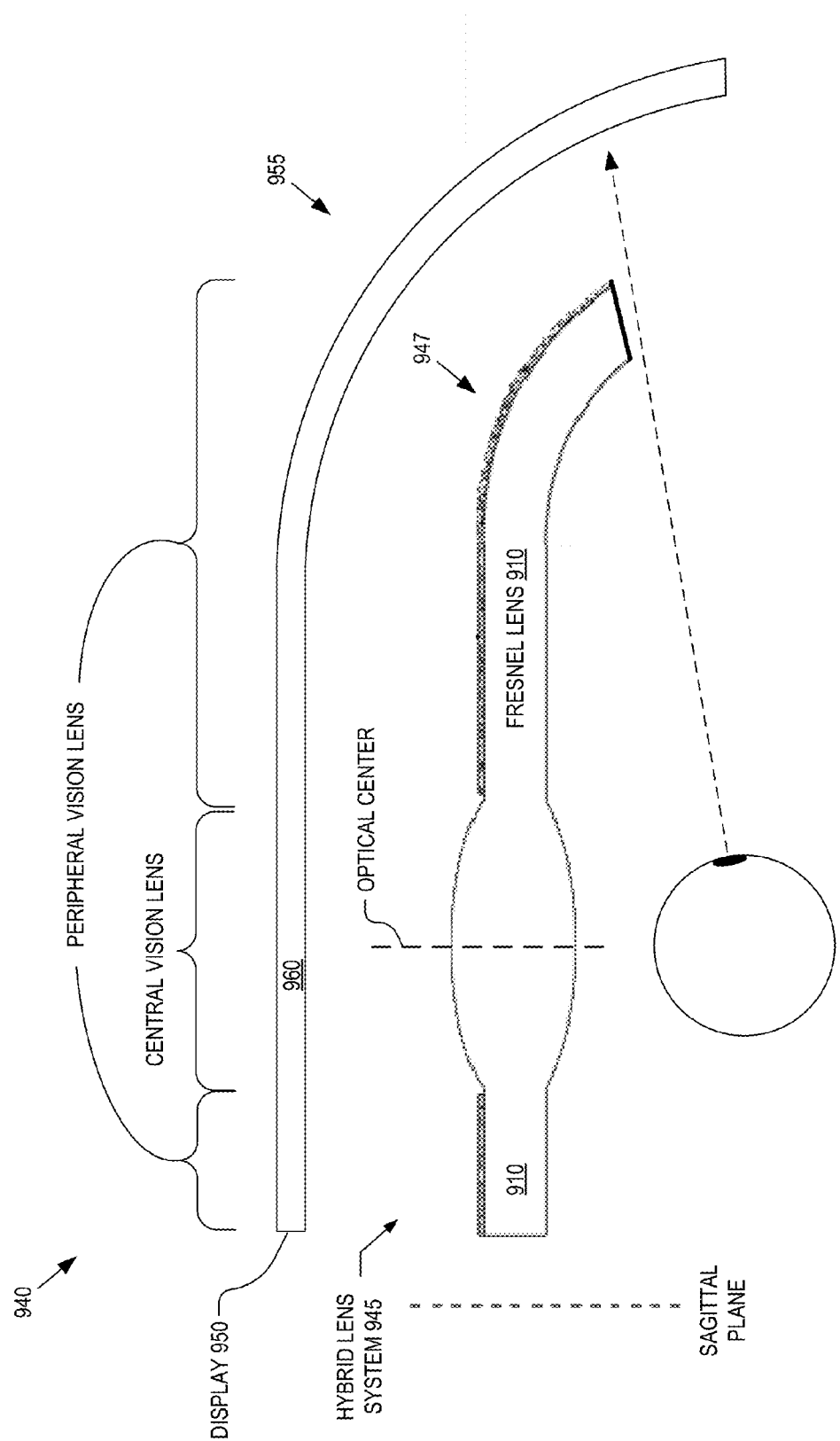
FIG. 9C illustrates a head wearable display including a display having a curved section that extends beyond the hybrid lens system for extreme peripheral vision, in accordance with a sixth embodiment of the disclosure.

FIG. 9C illustrates a head wearable display 940 including a hybrid lens system 945 having a curved section 947 and a display 950 having a curved section 955, in accordance with an embodiment of the disclosure. The illustrated display 950 includes a flat section 960 and curved section 955 that extends beyond the curved section 947 of hybrid lens system 945 so that display 950 may be viewed directly without any lens, or through clear plastic. In such an embodiment, display 950 is extended to a peripheral region of the FOV where the eye has so little peripheral resolution such that merely motion and awareness of light is detected. In this extreme peripheral region no lensing may be necessary. This is analogous to the image presented by prescription eyewear when looking beyond the outer edge of the lens. In such a case the peripheral image is out of focus, but it does not detract from a feeling of presence.

The brain perceives depth of objects from a number of cues. One cue is termed the accommodation distance—the distance at which the eye focuses. The brain is able to interpret ciliary muscle cues needed to obtain this focus and develop an estimate of distance from these focusing cues originating at the eye. A second cue is obtained by interpreting the extraocular muscle motion needed to turn the eyes so that gaze of both eyes converges on an object so as to fuse the perceived images of the left and right eye. This second distance cue is based on the angle to which the eyes must turn to place the object of interest on the fovea, and this perceived distance is called the vergence distance.

One of the known problems in conventional stereo/3D VR systems is the difference between vergence and accommodation distances. For example, some conventional 3D systems place the image plane at infinity and provide depth cues by vergence. This can lead to discomfort for the user. One way of reducing or eliminating accommodation vergence conflict is by adjusting the power of the VR system lens, which changes the image distance. Variable diopter lenses are known. If the eye gaze direction is known from eye tracking or can be estimated based on VR scene and objects of interest, then the vergence distance can be determined or estimated. An adjustable power lens can then be set to a focal length such that the accommodation distance equals the vergence distance, in this way eliminating accommodation-vergence disparity.

The equation that specifies the relationship between object distance $s_1$, image distance $s_2$, and focal length f is:

$$1/f = 1/s_1 + 1/s_2.$$

Employing the sign conventions appropriate for a magnifier system of the type discussed here yields:

$$1/f = 1/|s_1| - 1/|s_2|, \text{ or}$$

$$|s_2| = 1/\{-1/f + 1/|s_1|\}.$$

If the focal length is fixed, the image distance can alternatively be changed by adjusting the optical distance between the lens and the display pixel plane. By optical distance, OD, we mean the physical distance, PD, corrected for index of refraction n of the media between the lens and the pixel plane (for example, a layer of glass).

$$OD = n \cdot PD.$$

This distance is also known as the optical path length. We can vary this distance by at least the following three options: (1) moving the display, (2) interposing an optical material with a variable index of refraction (such as a liquid crystal), or (3) interposing an optical material with a variable physical thickness.

Figure 10:
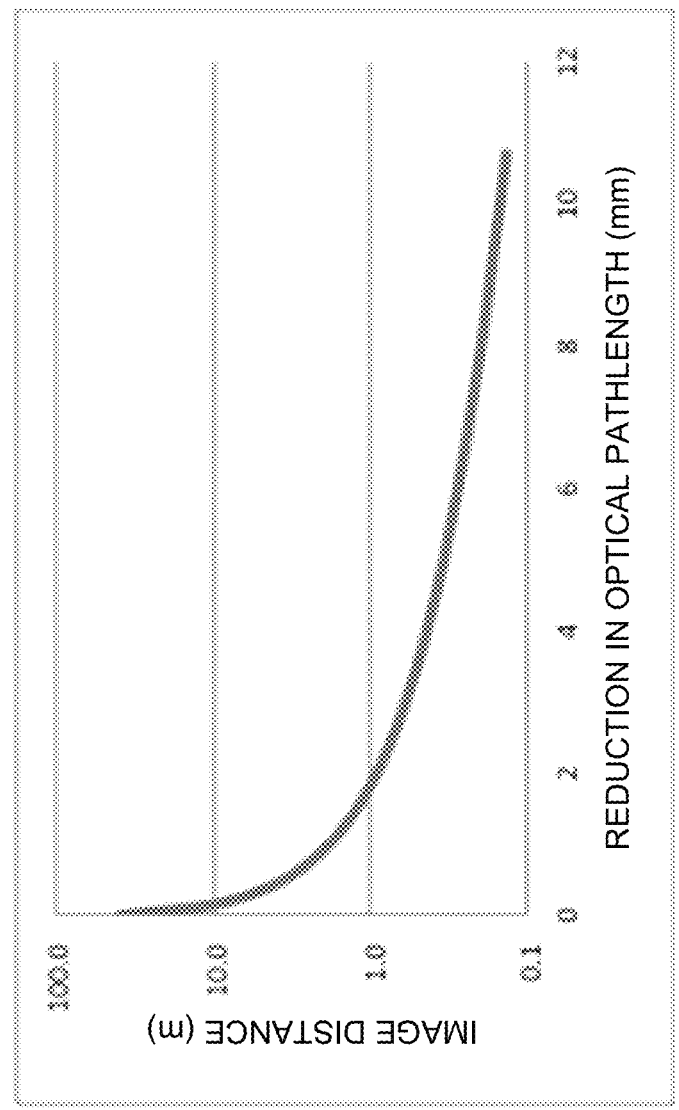
FIG. 10 is a chart illustrating a virtual image distance as a function of reduction in optical path length between a pixel plane and a lens, in accordance with an embodiment of the disclosure.

Eye tracking can be used to determine the convergence angle and from the angles and IPD, the convergence distance. Once convergence distance is known, accommodation distance can be adjusted to match. For example, if the focal length of the lens system is fixed at 44 mm, and the initial optical distance between the pixel plane and the lens is 43.95 mm, the image distance will be 38.7 m. FIG. 10 includes a chart illustrating the virtual image distance as a function of reduction in optical path length between the pixel plane and the lens. If the optical path length is reduced by 2 mm, the image is moved from 38.7 m to 1 m. A reduction of 4 mm reduces the distance of the image to 40 cm. Such a system could use about 10 mm of translation of the display to move the image from 38.8 m to 10 cm. Flexible displays have been developed, which would allow only part of the display to be moved. Thus, the image distance could be adjusted by moving the edge of the display nearest the nose by a few millimeters.

Figure 11:
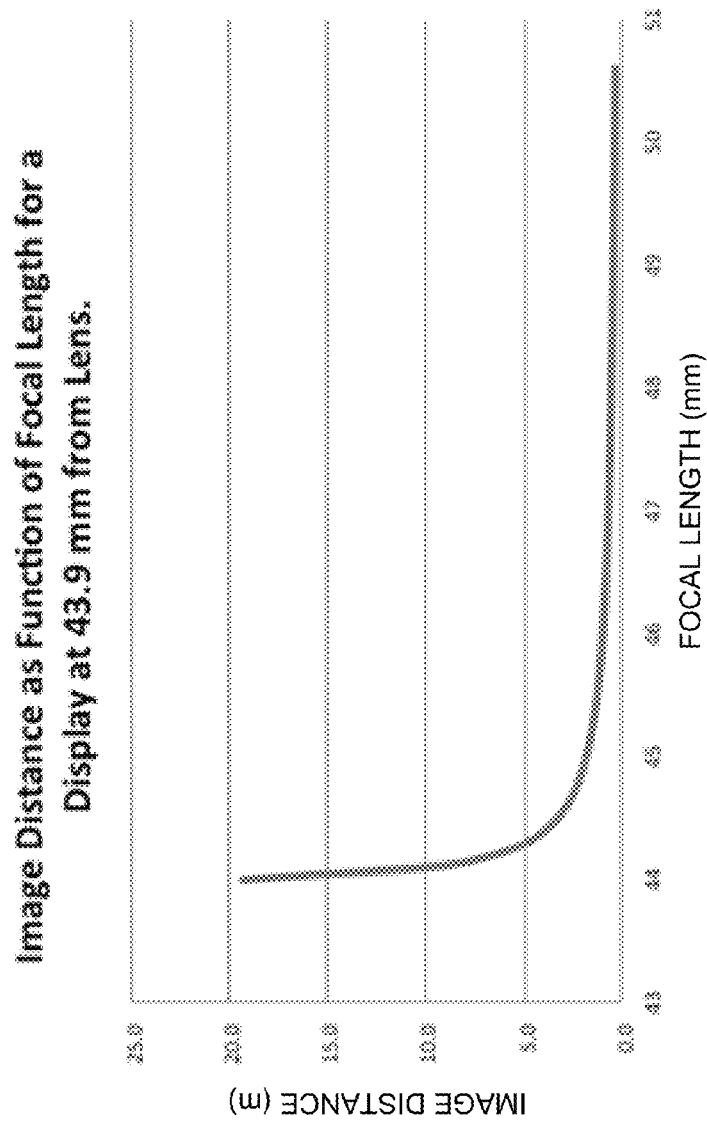
FIG. 11 is a chart illustrating an image distance as a function of focal length for a display placed at 43.9 mm from a lens, in accordance with an embodiment of the disclosure.

Another method of reducing accommodation-vergence conflict is based on adjusting the focal length of the lens. Such adjustable lenses are known and can be combined with the hybrid lens systems described above to form a lens with adjustable power. The vergence distance is determined from eye tracking, and the focal length of the lens is adjusted to obtain the appropriate accommodation distance. FIG. 11 includes a chart illustrating the image distance as a function of focal length for a display placed at 43.9 mm from the lens. As the focal length is increased from 44 mm to 50 mm, the image is moved from 19 m to 0.36 m. This is obtained by an increase in the radius of curvature of the adjustable lens.

A passive method of reducing accommodation-vergence disparity is obtained by using a modification of a progressive lens that has been in use in ophthalmics for correction of presbyopia. Ophthalmic progressive lenses have focal length that varies as the eye rotates from the center of the lens toward the bottom of the lens, and toward the nose. By adding optical power as the convergence is increased, objects that are closer are brought into focus. This principle can be modified for reducing accommodation-vergence conflict.

Figure 12:
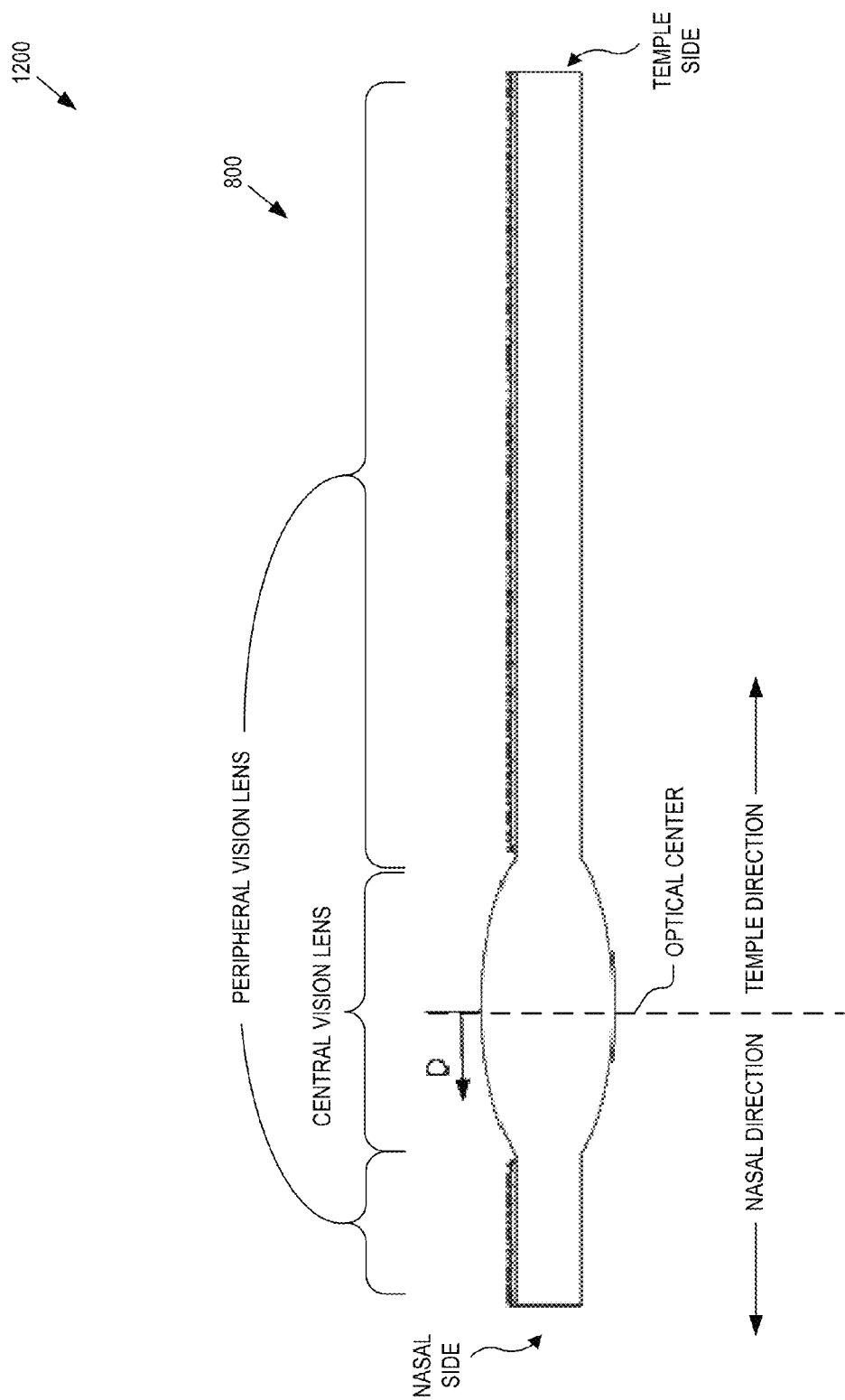
FIG. 12 illustrates a hybrid lens system in which optical power is varied radially in the nasal direction, in accordance with an embodiment of the disclosure.

FIG. 12 illustrates a hybrid lens system 1200 in which the optical power of the peripheral vision lens is varied radially in the nasal direction indicated by D. Recall that the position of the virtual image is given by:

$$|s_2| = -1/\{1/f - 1/|s_1|\},$$

where $s_1$ is the distance from the display to the lens, and $s_2$ is the distance from the image to the lens. Assuming $s_1$ is fixed, if the object is viewed through a section of the lens for which f is smaller than the center, then $s_2$ is smaller, meaning that the image is brought closer. Referring again to FIG. 12, if the focal length decreases with distance D from the center of hybrid lens system 1200 toward the nose, the image is brought closer as the user looks more in the nasal direction.

Figure 13:
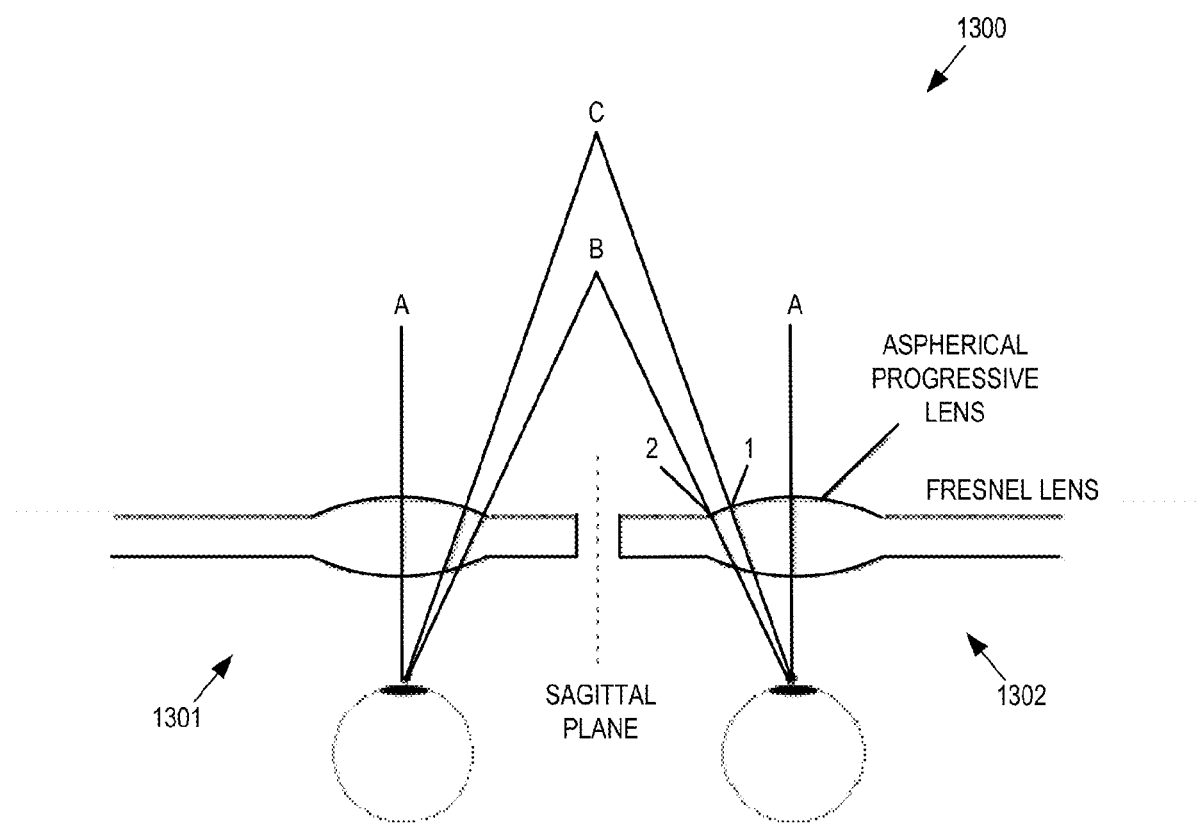
FIG. 13 illustrates a binocular hybrid optical system including left and right hybrid lenses each having a variable focal length, in accordance with an embodiment of the disclosure.

FIG. 13 illustrates a binocular hybrid optical system 1300 including left and right hybrid lenses 1301 and 1302, respectively, in accordance with an embodiment of the disclosure. When the user looks at distant object A, the gaze angles of the two eyes are parallel and directed through the central vision lenses. If the focal length of the optical centers of the central vision lenses is approximately the distance to the display, the user sees an image at an accommodation distance of optical infinity which is consistent with a convergence angle of zero. When the user looks at an object at point C, the user's gaze is necessarily through the central vision lenses at point 1. If the focal length at point 1 is larger than in the center, the accommodation distance is moved from infinity to point C, even though the display position is unchanged. If the lens is designed so that looking through point 2 has an even higher focal length so that the accommodation distance of the object is moved to point B. In this way, the convergence distance and accommodation distance are made to correspond.

For objects that are viewed by turning one eye toward the temple, a disparity will still be present: the eye turning toward the nose will have a closer accommodation distance than the eye turning toward the temple. Yet, if the head is subsequently turned to center the image on the sagittal plane (which is the natural way to view objects), the disparity will be absent. Therefore, since centering the object of interest in the binocular field is the natural way to view images, this technique cures the disparity for the most natural way of viewing close objects.

Figure 14:
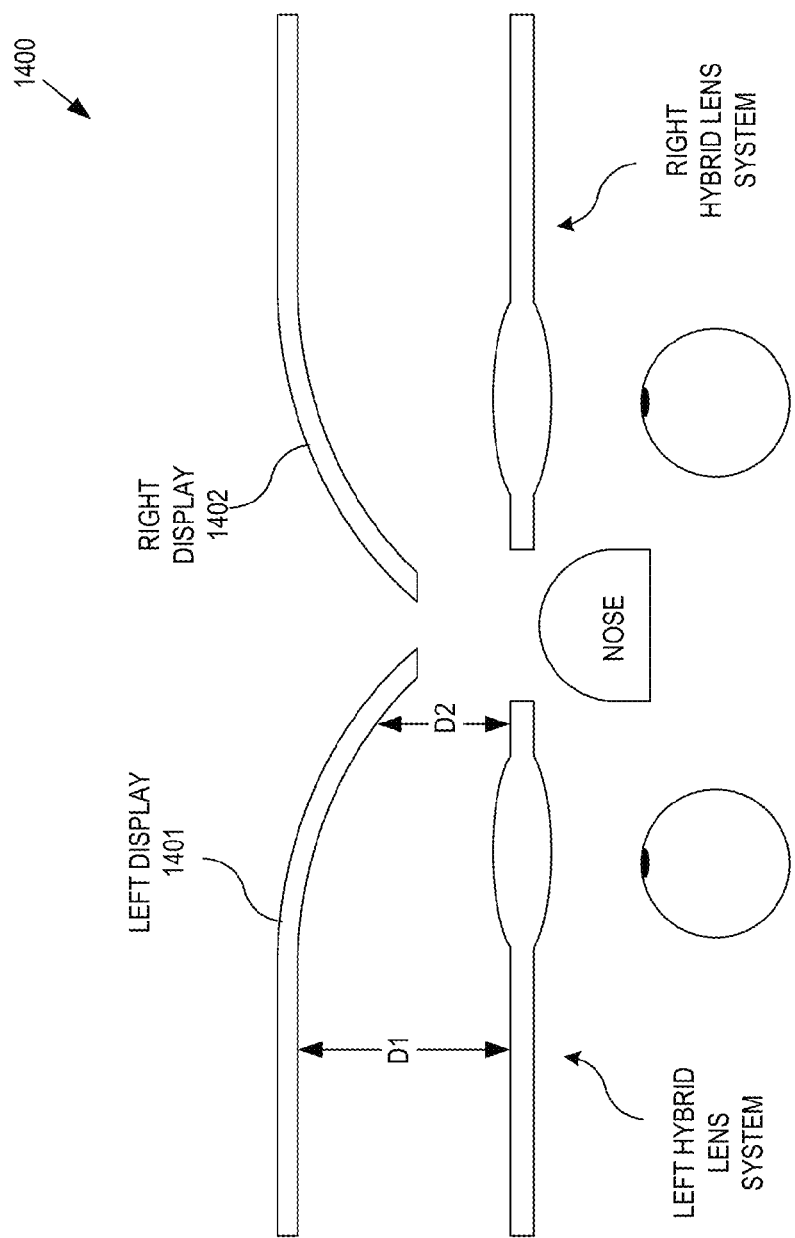
FIG. 14 illustrates a binocular head wearable display including flexible displays curved inward towards the nose to remove the conflict between vergence and accommodation distances, in accordance with an embodiment of the disclosure.

FIG. 14 illustrates a binocular head wearable display 1400 including flexible displays 1401 and 1402, in accordance with an embodiment of the disclosure. An alternative to a hybrid lens system using a fixed progressive focal length is to use flexible displays 1401 and 1402 and curve the displays 1401 and 1402 slightly toward the nose, as illustrated in FIG. 14. Since separation D2 is less than separation D1, the resultant image distance decreases as the direction of gaze is moved toward the nose. The curvature of displays 1401 and 1402 can be matched to remove the conflict between the vergence distance and the accommodation distance.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A hybrid optical system for a head wearable display, comprising:
    a central vision lens to approximately align with a cornea of a user and to provide lensing to a central vision of the user when the user is looking straight forward; and
    a peripheral vision lens, different than the central vision lens, to provide lensing having optical power to an extended field of view ("FOV") that extends angularly beyond the central vision lensed by the central vision lens when the user is looking straight forward,
    wherein the peripheral vision lens is disposed around the central vision lens,
    wherein the peripheral vision lens has a co-incident optical center with the central vision lens but the central vision lens is offset from a physical center of the peripheral vision lens,
    wherein the central vision lens comprises a refractive lens having two opposing sides that are both curved surfaces and the two opposing sides along with the peripheral vision lens are molded into a single piece of plastic.

2. The hybrid optical system of claim 1, wherein the peripheral vision lens comprises a Fresnel lens.

3. The hybrid optical system of claim 1, wherein the central vision lens comprises a singlet lens.

4. The hybrid optical system of claim 3, wherein the central vision lens further comprising at least one additional lensing layer disposed over a frontside or a backside of the singlet lens.

5. The hybrid optical system of claim 1, wherein the central vision lens and the peripheral vision lens are molded into a single piece of plastic.

6. The hybrid optical system of claim 1, wherein the central vision lens comprises an optical insert disposed within a portion of the peripheral vision lens, wherein the optical insert is fabricated from a different material than the peripheral vision lens.

7. The hybrid optical system of claim 1, wherein the central vision lens comprises at least one of a spherical lens, an aspherical lens, a progressive lens, an achromatic lens, a diffractive optical element, or a hologram.

8. The hybrid optical system of claim 1, wherein the peripheral vision lens includes a nasal side and a temple side, wherein the peripheral vision lens curves inward along the temple side.

9. The hybrid optical system of claim 8, wherein the peripheral vision lens has a focal length that increases with offset distance from the central vision lens towards the temple side.

10. The hybrid optical system of claim 8, wherein the peripheral vision lens is planar on the nasal side of the central vision lens.

11. The hybrid optical system of claim 8, wherein the peripheral vision lens curves inward along the nasal side.

12. The hybrid optical system of claim 1, wherein the peripheral vision lens has a focal length that decreases with radial distance from the optical center of the central vision lens towards a nasal direction.

13. The hybrid optical system of claim 1, wherein the hybrid optical system is asymmetrical with the central vision lens position closer to a nasal side of the peripheral vision lens than to a temple side of the peripheral vision lens.

14. The hybrid optical system of claim 1, wherein the central vision lens provides higher optical acuity than the peripheral vision lens.

15. A head wearable display, comprising:
    a display panel; and
    a hybrid optical lens system disposed along an eye-ward side of the display panel and including:
        a central vision lens to approximately align with a cornea of a user and to provide lensing to a central vision of the user when the user is looking straight forward; and
        a peripheral vision lens, different than the central vision lens, to provide lensing having optical power to an extended field of view ("FOV") that extends angularly beyond the central vision lensed by the central vision lens when the user is looking straight forward,
    wherein the peripheral vision lens is disposed around the central vision lens,
    wherein the peripheral vision lens has a co-incident optical center with the central vision lens but the central vision lens is offset from a physical center of the peripheral vision lens, wherein the central vision lens comprises a refractive lens having two opposing sides that are both curved surfaces and the two opposing sides along with the peripheral vision lens are molded into a single piece of plastic.

16. The head wearable display of claim 15, wherein the display panel comprises a curved display panel and wherein the peripheral vision lens is disposed along a curved substrate.

17. The head wearable display of claim 16, wherein the curved display panel has a first curved portion along a temple side that extends beyond a second curved portion of the peripheral vision lens such that a wearer of the head wearable display can directly view the first curved portion of the curved display panel without looking through the hybrid optical lens system.

18. The head wearable display of claim 16, wherein the display panel includes a planar portion disposed in front of the central vision lens and a curved portion disposed in front of the peripheral vision lens that is on a temple side of the central vision lens.

19. The head wearable display of claim 18, wherein the peripheral vision lens is disposed along a substrate having a first portion adjacent to the central vision lens and a second portion that is curved on the temple side of the central vision lens.

20. The head wearable display of claim 15, wherein the display panel is planar and wherein the peripheral vision lens has a curved portion disposed on a temple side of the central vision lens.

21. The head wearable display of claim 20, wherein the curved portion of the peripheral vision lens has a focal length that increases with radial distance from a center of the central vision lens.

22. The head wearable display of claim 15, wherein the head wearable display comprises a binocular head wearable display including a pair of display panels and a pair of hybrid optical lens systems.

23. The head wearable display of claim 15, wherein a first focal length of the hybrid optical lens system through the optical center of the central vision lens corresponds to a separation distance between the hybrid optical lens system and the display panel while a second focal length of the hybrid optical lens system through a region of the hybrid optical lens system between the optical center and a nasal side of the hybrid optical lens system has a second focal length longer than the first focal length to compensate for a discrepancy between accommodation and vergence.

24. The hybrid optical system of claim 1, wherein the peripheral vision lens has different optical power than the central vision lens and wherein the peripheral vision lens is a different type of lens than the central vision lens.

* * * * *